(12) United States Patent
Shinoda

(10) Patent No.: US 7,367,273 B2
(45) Date of Patent: May 6, 2008

(54) DIAGNOSTIC TABLE

(75) Inventor: Katsuaki Shinoda, Kuroiso (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 471 days.

(21) Appl. No.: 10/965,831

(22) Filed: Oct. 18, 2004

(65) Prior Publication Data

US 2005/0129181 A1    Jun. 16, 2005

(30) Foreign Application Priority Data

Nov. 21, 2003   (JP)  ............................. 2003-392087

(51) Int. Cl.
   *A47B 11/00*   (2006.01)
(52) U.S. Cl. ..................................... 108/143
(58) Field of Classification Search ................ 108/143, 108/137; 5/600, 601, 602; 378/209, 20, 378/208; 600/425
   See application file for complete search history.

(56) References Cited

U.S. PATENT DOCUMENTS 4,131,802 A * 12/1978 Braden et al. ................ 378/20
5,040,431 A *  8/1991 Sakino et al. ................ 108/143
5,066,915 A * 11/1991 Omori et al. ................ 324/318
5,204,629 A *  4/1993 Ueyama ...................... 600/415
5,596,779 A *  1/1997 Meek ............................ 5/600
5,960,054 A *  9/1999 Freeman et al. ............... 378/4
6,615,428 B1 * 9/2003 Pattee ........................... 5/601
6,637,056 B1 * 10/2003 Tybinkowski et al. ...... 378/209

FOREIGN PATENT DOCUMENTS

JP          6-3306      1/1994
JP          7-88102     4/1995

* cited by examiner

*Primary Examiner*—Jose V. Chen
(74) *Attorney, Agent, or Firm*—Oblon, Spivak, McClelland, Maier & Neustadt, P.C.

(57) ABSTRACT

A diagnostic table for a medical imaging apparatus includes a sliding command input device by which a sliding command is configured to be input to produce a sliding movement of a tabletop, a first detector configured to detect sliding movement of the tabletop, a second detector configured to detect input of the sliding command, a stopper coupled to the tabletop and configured to prevent the tabletop from sliding, and a controller coupled to the first and second detectors and the stopper, the controller configured to determine a fault condition when the first detector detects sliding movement of the tabletop inconsistent with the command detected by the second detector and to activate the stopper to prevent the sliding movement of the tabletop upon determining existence of the fault condition.

20 Claims, 8 Drawing Sheets

DIAGNOSTIC TABLE

CROSS-REFERENCE TO RELATED APPLICATION

This application claims the benefit of priority of Japanese patent application no. P2003-392087, filed on Nov. 21, 2003, the disclosure of which is incorporated by reference herein in its entirety.

BACKGROUND OF THE INVENTION

1. Field of the Invention

The present invention relates to a diagnostic table which can be tilted, as well as a medical imaging apparatus including the diagnostic table.

2. Discussion of the Related Art

In a medical imaging apparatus such as, for example, an X-ray diagnosis apparatus, a diagnostic table is used as a part of or independent of the medical imaging apparatus. A patient who to be imaged by the medical imaging apparatus typically lies on a tabletop of the diagnostic table. One known tabletop is usually controlled to change its position so that the patient can be positioned appropriately to be imaged by the medical imaging apparatus. The tabletop may be moved in various directions, for example, upwards and downwards, along its longitudinal direction or a body axis of the patient lying on the tabletop, and/or along a left/right direction of the patient lying on the tabletop (i.e., a lateral direction). The tabletop may also be rotated and/or be tilted. An operator of the diagnostic table typically operates an operation unit of the diagnostic table so that the tabletop may be adjusted to an appropriate position for imaging the patient by a motor provided in the diagnostic table.

When power is supplied to the diagnostic table, a magnetic brake fixes the position of the tabletop. If the operator, for example, grasps a grip of the tabletop when the tabletop is kept horizontally, a switch provided in the grip is activated in response to the grasp. Accordingly, the magnetic brake is released so that the operator can manually move the tabletop horizontally along the longitudinal direction and the lateral direction. Such direction movement is referred to as a floating operation. Further, in response to the release of the magnetic brake, the operator can rotate the tabletop horizontally. Such a rotation is referred to as a panning operation.

A first gear, which can be activated by a gear motor, is also provided in the diagnostic table. The first gear may be formed like a disk and have teeth along an edge of the disk. The diagnostic table further includes the second gear magnetically coupled to the first gear when the second gear is engaged with the first gear. The second gear is formed in a toric shape and has inner teeth along the inside of the toric shape. The first gear can be inserted into the inside of the second gear. The teeth of the first gear are engaged with the inner teeth of the second gear. Such a relationship between the first gear and the second gear may be called a tooth clutch. The second gear also has outer teeth along an edge of the toric shape. The tabletop has teeth on the side opposite to the side where the patient lies. The outer teeth of the second gear may be engaged with the teeth of the tabletop.

In the above configuration, when the operator activates a tabletop tilt button to tilt the tabletop, the first gear is inserted into the inside of the second gear, and the teeth of the first gear are magnetically coupled to and engaged by the teeth of the second gear. Also in response to the activation of the tabletop tilt button, another motor (tilt motor) is activated to tilt the tabletop. During tilting, the tabletop is fixed by the magnetic brake and the tooth clutch operation at a position determined before tilting. When the tilt position is determined, the tilt motor is stopped in response to deactivation of the tabletop tilt button by the operator. If it is necessary to adjust a position of the tabletop along the tilt, that is, for example, along the longitudinal direction of the tabletop, a tabletop longitudinal movement button is activated by the operator. In response to the activation, the gear motor is activated (or rotated) to rotate the first gear while the magnetic brake is released from the tabletop. Since the first gear has been already engaged with the second gear, the tabletop is moved along the longitudinal direction by the second gear, which is rotated by the first gear. Consequently, the patient lying on the tabletop can be positioned appropriately for imaging by the X-ray diagnosis apparatus. After the movement along the longitudinal direction, the magnetic brake is activated again.

After imaging, the tabletop may be tilted back to the horizontal position in a manner similar to the above description, and the engagement of the tooth clutch is released. Also the magnetic brake can be released to allow the floating operation and the panning operation. After the power supply to the diagnostic table is terminated, the magnetic brake may attract the tabletop with its remaining magnetic force.

Examples of the above-described diagnostic table are described in Japanese patent application publication nos. PH07-88102 and UH06-3306.

When the patient is lying on the tabletop, the gross weight of the tabletop and the patient may be approximately one hundred to one hundred and fifty kilograms, or more. Such weight is applied to the magnetic brake and the tooth clutch. When the tabletop is tilted, if a deficiency exists within the tooth clutch and/or the gear motor such that the teeth of the first gear and the inner teeth of the second gear cannot satisfactorily engage with one another, the magnetic brake may not be able to support the weight when the weight is greater than a predetermined maximum weight of the magnetic brake. The deficiency may be, for example, worn-out of the teeth of the first gear, the inner teeth of the second gear, the outer teeth of the second gear, a gear of the gear motor, the gear of the tabletop, and/or reduction gear(s) coupled to the motor if provided. Another possible deficiency may be damage to one or more signal lines to the gear motor, leakage of oil for the reduction gear(s), and/or the like. Also the deficiency may be a breakdown of the gear motor, a breakdown of a reduction unit connected to the gear motor due to oil leakage, a breakdown of internal coils which control the coupling of the gears in the tooth clutch, and/or a break of one or more power lines to the internal coils.

As a result, the tabletop cannot be fixed, and may slide. The tabletop is likely to slide to a greater degree as the tabletop is increasingly tilted.

It is important to prevent or limit this sliding to ensure the safety of the patient. One way to prevent the sliding may be an installation of another tooth clutch. Such a solution, however, complicates the diagnostic table. Further, the tabletop may still slide even after providing another tooth clutch, depending on the weight and a tilted angle. Particularly, when there is deficiency in the gear of the tabletop, the provision of another tooth clutch may not prevent the tabletop from sliding.

SUMMARY OF THE INVENTION

According to one aspect of the present invention there is provided a diagnostic table for a medical imaging apparatus including a sliding command input device by which a sliding command is configured to be input to produce a sliding movement of a tabletop, a first detector configured to detect sliding movement of the tabletop, a second detector configured to detect input of the sliding command, a stopper coupled to the tabletop and configured to prevent the tabletop from sliding, and a controller coupled to the first and second detectors and the stopper, the controller configured to determine a fault condition when the first detector detects sliding movement of the tabletop inconsistent with the command detected by the second detector and to activate the stopper to prevent the sliding movement of the tabletop upon determining existence of the fault condition.

In another embodiment of the invention the second detector is configured to detect a presence of the sliding command, and the controller is configured to determine a nonrequested movement fault condition when the first detector detects sliding movement of the tabletop inconsistent with the presence of the sliding command detected by the second detector and to activate the stopper upon determining the existence of the nonrequested movement fault condition.

In still another embodiment of the invention, the first detector is configured to detect a direction of sliding movement, the sliding command input device is configured to receive an input sliding direction command, the second detector is configured to detect the sliding direction command, and the controller is configured to determine a sliding direction fault condition when the first detector detects sliding movement of the table top in a direction inconsistent with the sliding direction command detected by the second detector and to activate the stopper upon determining the existence of the sliding direction fault condition.

In still another embodiment of the invention, the first detector is configured to detect a speed of sliding movement, the sliding command input device is configured to receive an input sliding speed command, the second detector is configured to detect the sliding speed command, and the controller is configured to determine a sliding speed fault condition when the first detector detects sliding movement of the tabletop at a speed greater than the sliding speed command detected by the second detector and to activate the stopper upon determining the existence of the sliding speed fault condition.

In still another embodiment of the invention there is provided a motor configured to slide the tabletop, wherein the first detector is configured to detect a speed of sliding movement, and the controller is configured to determine an excessive sliding speed fault condition when the first detector detects sliding movement of the tabletop at a speed greater than a maximum speed at which the motor is configured to slide the table and to activate the stopper upon determining the existence of the excessive sliding speed fault condition.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

An embodiment of a diagnostic table and a medical imaging apparatus including the diagnostic table is described with reference to the accompanying drawings. In the following description, an X-ray diagnosis apparatus is shown as an example of the medical imaging apparatus, particularly, when the X-ray diagnosis apparatus is used for an examination in which a flow of a contrast agent is controlled in accordance with a force of gravitation. For controlling the flow of the contrast agent in accordance with the force of gravitation, a tabletop of the diagnostic table is usually tilted, which results in tilting of a patient. In this case, a gas such as, for example, carbon dioxide is typically used as the contrast agent. If the gas is more dense than blood, the gas flows down through blood vessels when the tabletop is tilted. If the gas is less dense than blood, the gas flows up through blood vessels when the tabletop is tilted.

Figure 1:
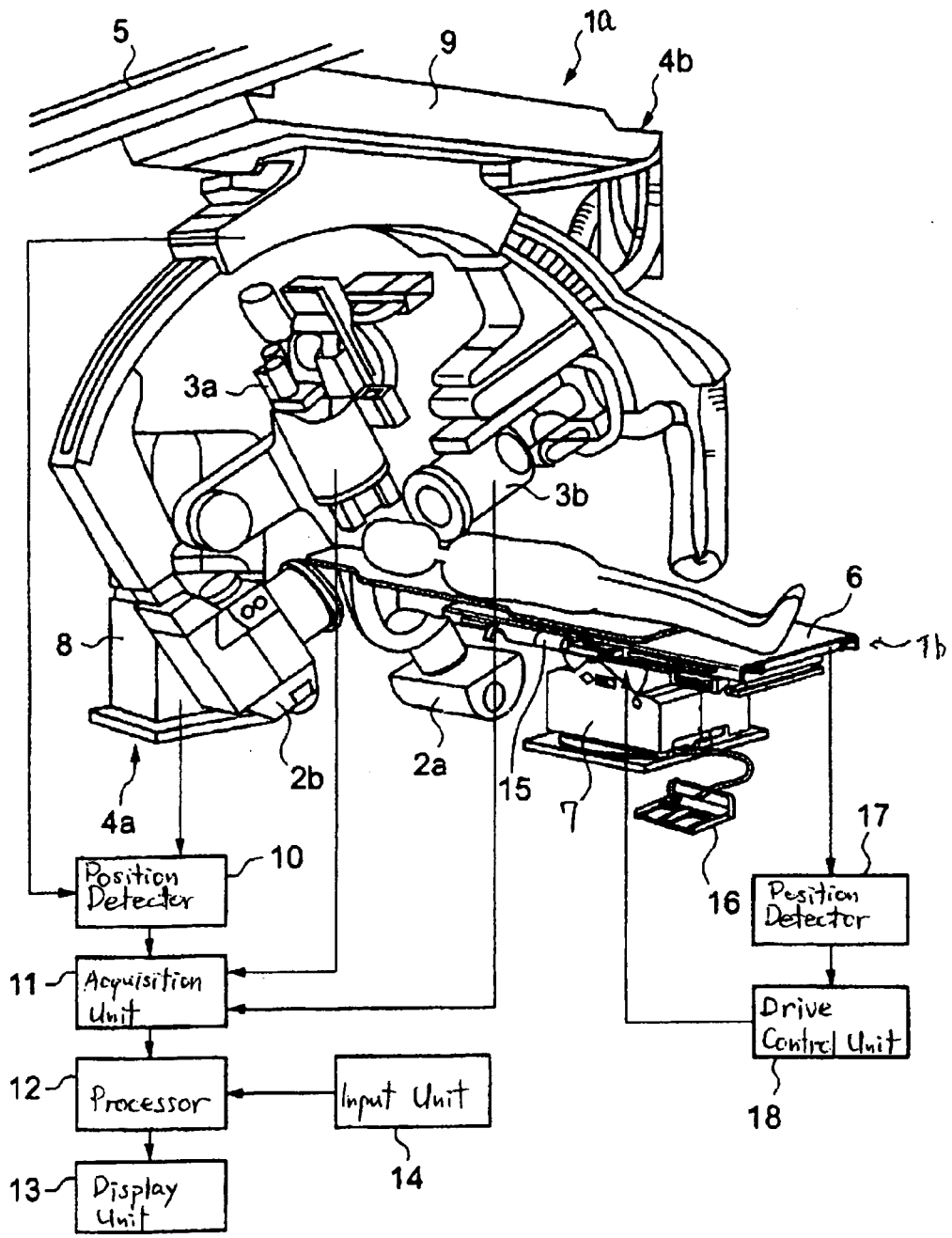
FIG. 1 is a schematic showing an example of an X-ray diagnosis apparatus according to an embodiment of the present invention.

FIG. 1 is a schematic showing an example of an X-ray diagnosis apparatus according to an embodiment of the present invention. As shown in FIG. 1, the X-ray diagnosis apparatus includes a main body 1a and a diagnostic table 1b.

The main body 1a includes the first imaging unit 4a and the second imaging unit 4b. The first imaging unit 4a includes an arm formed, for example, in a shape of a letter 'C' (referred to as a C-arm) and the C-arm has an X-ray tube 2a at one end and an X-ray detector 3a at the other end. The X-ray tube 2a and the X-ray detector 3a face or oppose each other so that X-ray generated from the X-ray tube 2a can be detected by the X-ray detector 3a. One or both of the X-ray tube 2a and the X-ray detector 3a may be moved towards and away from each other. The X-ray detector 3a may be formed in a two-dimensional manner.

Similarly, the second imaging unit 4b includes an arm formed, for example, in a shape of a Greek letter, omega ('ω') (referred to as an ω-arm) and the ω-arm has an X-ray tube 2b at its one end and an X-ray detector 3b at the other end. The X-ray tube 2b and the X-ray detector 3b face to each other so that X-ray generated from the X-ray tube 2b can be detected by the X-ray detector 3b. One or both of the X-ray tube 2b and the X-ray detector 3b may be moved towards and against to the other or to each other. The X-ray detector 3b may be formed in a two-dimensional manner.

The first imaging unit 4a further includes a supporting portion 8 which rotatably supports the C-arm. The supporting portion 8 may be fixed on the floor or provided movably along the floor. The C-arm may also be slid along its arc. The second imaging unit 4b includes a supporting portion 9 which supports the ω-arm in a slidable manner along an arc of the ω-arm. The supporting portion 9 moves along rails 5 fixed to the ceiling. The supporting portion 9 may alternatively be fixed to the ceiling.

The main body 1a further includes a position detector 10, an acquisition unit 11, a processor 12, a display unit 13, and an input unit 14. The position detector 10 detects a position and a rotation angle of the C-arm and a position and a rotation angle of the ω-arm. The acquisition unit 11 acquires image data detected by the X-ray detectors 3a and 3b and stores the acquired image data, for example, temporarily. The processor 12 may include a central processing unit (CPU) and a memory storing processing programs needed for various types of image processing on the image data acquired by the acquisition unit 11. The display unit 13 displays the processed image data as images. The display unit 13 may alternatively be provided independently of the main body 1a as a personal computer or a workstation. The input unit 14 may include a mouse, a trackball, a keyboard, and/or the like and be used to input data and/or instructions to the main body 1a.

The diagnostic table 1b includes a tabletop 6, a supporting unit 7, an operation unit 15, a foot switch 16, a position detector 17, and a drive control unit 18. The diagnostic table 1b may include a magnetic brake and tooth clutch (not shown).

A patient to be imaged by the X-ray diagnosis apparatus lies on the tabletop 6. The tabletop 6 can be moved along its longitudinal direction and its lateral direction. The tabletop 6 can also be moved upwards and downwards, and can be tilted to orient a patient's head up and feet down, and vice versa. The tilting operation may further or alternatively be performed to orient a patient's left side up and right side down, and vice versa. When the tabletop 6 is positioned horizontally, the tabletop 6 may be manually moved by a floating operation and a panning operation.

The tabletop 6 is supported by the supporting unit 7 which may be fixed on the floor. The operation unit 15 includes, for example, switches, buttons, levers, and/or the like to input instructions to the diagnostic table 1a. The movement of the tabletop 6 is also controlled by the instructions input from a tabletop tilt button, a tabletop longitudinal movement button, a tabletop vertical movement button, and the like of the operation unit 15. The foot switch 16 may be used to instruct radiography to the main body 1a through the diagnostic table 1b. The position detector 17 may include, for example, one or more encoders and/or one or more potentiometers and detects a position, a tilting angle, and a rotation angle of the tabletop 6. Detected information may be stored in a memory (not shown) under a control of the drive control unit 18. The drive control unit 18 may also control the magnetic brake and the tooth clutch in accordance with the position and angle information detected by the position detector 17, the instructions input from the operation unit 15, the switching to allow the floating and panning operations, and the like.

When the magnetic brake and the tooth clutch are used in the diagnostic table 1b, the basic operation of the diagnostic table 1b for the imaging examination may be as follows. When power is supplied to the diagnostic table 1b, the magnetic brake that may be provided in the supporting unit 7 is energized to attract the tabletop 6, thereby fixing the position of the tabletop 6. If an operator such as, for example, a doctor or a radiological technologist, grasps a grip of the tabletop 6 when the position detector 17 detects that the tabletop 6 is in a horizontal position, a switch provided in the grip is activated in response to the grasp. Accordingly, the attraction by the magnetic brake is released so that the operator can perform the floating operation and/or the panning operation. The patient lying on the tabletop 6 can be moved to a position approximately corresponding to an imaging position. The operator may then operate the operation unit 15 so that the tabletop 6 is lifted up to a position closer to the appropriate position.

In the diagnostic table 1b (or in the supporting unit 7), there is provided the first gear which can be activated by a gear motor also provided. The first gear may be formed like a disk and have teeth along an edge of the disk. The diagnostic table 1b includes the second gear which is magnetically coupled to the first gear when the second gear is engaged with the first gear. The second gear is formed in a toric shape and has inner teeth along the inside of the toric shape. The first gear can be inserted into the inside of the second gear. The teeth of the first gear are engaged with the inner teeth of the second gear as the tooth clutch. The second gear also has outer teeth along an edge of the toric shape. The tabletop 6 has teeth on the side opposite to the side where the patient lies. The outer teeth of the second gear may usually be engaged with the teeth of the tabletop 6.

When the operator activates the tabletop tilt button to tilt the tabletop 6, the first gear is inserted into the inside of the second gear, and accordingly is magnetically coupled to and engaged by the teeth with the second gear. Also in response to the activation of the tabletop tilt button, another motor (tilt motor) provided in the diagnostic table 1b (or in the supporting unit 7) is activated to tilt the tabletop 6. During tilting, the tabletop 6 is fixed at a position by the magnetic brake and the tooth clutch operation determined before tilting. When the tilt position is determined, the operator deactivates the tabletop tilt button so that the tilt motor is stopped. If the operator desires to adjust a position of the tabletop along the tilt, that is, for example, along the longitudinal direction of the tabletop 6, the operator activates the tabletop longitudinal movement button. In response to the activation, the gear motor is activated (or rotated) to rotate the first gear while attraction of the magnetic brake is released from the tabletop 6. Since the first gear has been engaged with the second gear, the tabletop 6 is moved along the longitudinal direction by the second gear which is rotated by the first gear. Consequently, the patient lying on the tabletop 6 can be positioned appropriately for the imaging examination. After the movement along the longitudinal direction, the magnetic brake is activated again. In practice, the operator operates the input unit 15 to move the C-arm and the ω-arm and, if necessary, the X-ray tube 2a, the X-ray detector 3a, the X-ray tube 2b, and/or the X-ray detector 3b, in addition to the adjustment of the tabletop position. In combination of the adjustment in the main body 1a and the diagnostic table 1b, a target position of the patient for the imaging examination can be positioned appropriately in relationship with the X-ray tube 2a and the X-ray detector 3a, and the X-ray tube 2b and the X-ray detector 3b. A set of the X-ray tube 2a and the X-ray detector 3a may be placed perpendicular to a set of the X-ray tube 2b and the X-ray detector 3b.

The operator then operates the foot switch 16 to conduct the radiography. In response to the foot switch 16, the X-ray tube 2a and the X-ray tube 2b generate or radiate X-rays. The X-rays are detected by the X-ray detectors 3a and 3b. Each of the X-ray detectors 3a and 3b may include an image intensifier and a TV camera. The image intensifier may provide transmitted images obtained based on the X-ray generation as optical images. The TV camera images the optical images. The X-ray detectors 3a and 3b are not limited to the above, but may be formed as flat panel detectors, respectively. The flat panel detector has a structure in which a plurality of X-ray detection elements are arrayed in a two-dimensional manner, as disclosed, for example, in Japanese patent application publication no. PH08-332191.

When the radiography is conducted, the position detector 10 detects positions and angles of the first imaging unit 4a and the second imaging unit 4b. The detected position and angle information is acquired by and stored in the acquisition unit 11 with the image data detected by the X-ray detectors 3a and 3b.

The detected image data and the detected position and angle information are processed in the processor 12. The processor 12 performs, for example, reconstruction processing based on the detected image data and the detected position and angle information to prepare, for example, three dimensional image data or virtual endoscopic image data. In addition, for example, the processor 12 may also produce clinical analysis information of the patient based on the reconstructed image data and perform a subtraction processing, image superimposing processing, and/or image rotation processing. The processor 12 may further, for example, calculate and obtain a position and a direction of the target position (or a region of interest) of the patient on the image data. The display unit 13 displays such processed image data and the clinical analysis information.

Position information and numeral information to be displayed in the display unit 13 may be instructed or directly input from the input unit 14 to the processor 12. The operator may also input various instructions to the processor 12 from the input unit 14.

After the imaging examination, the tabletop 6 may be tilted back to the horizontal position and the engagement of the tooth clutch released. Also the magnetic brake is released to allow the floating operation and the panning operation. The operator may or may not perform the floating operation and/or the panning operation, and accordingly the patient can leave the tabletop 6. If the power supply to the diagnostic table 6 is terminated, the magnetic brake can attract the tabletop 6 with its remaining magnetic force.

Figure 2:
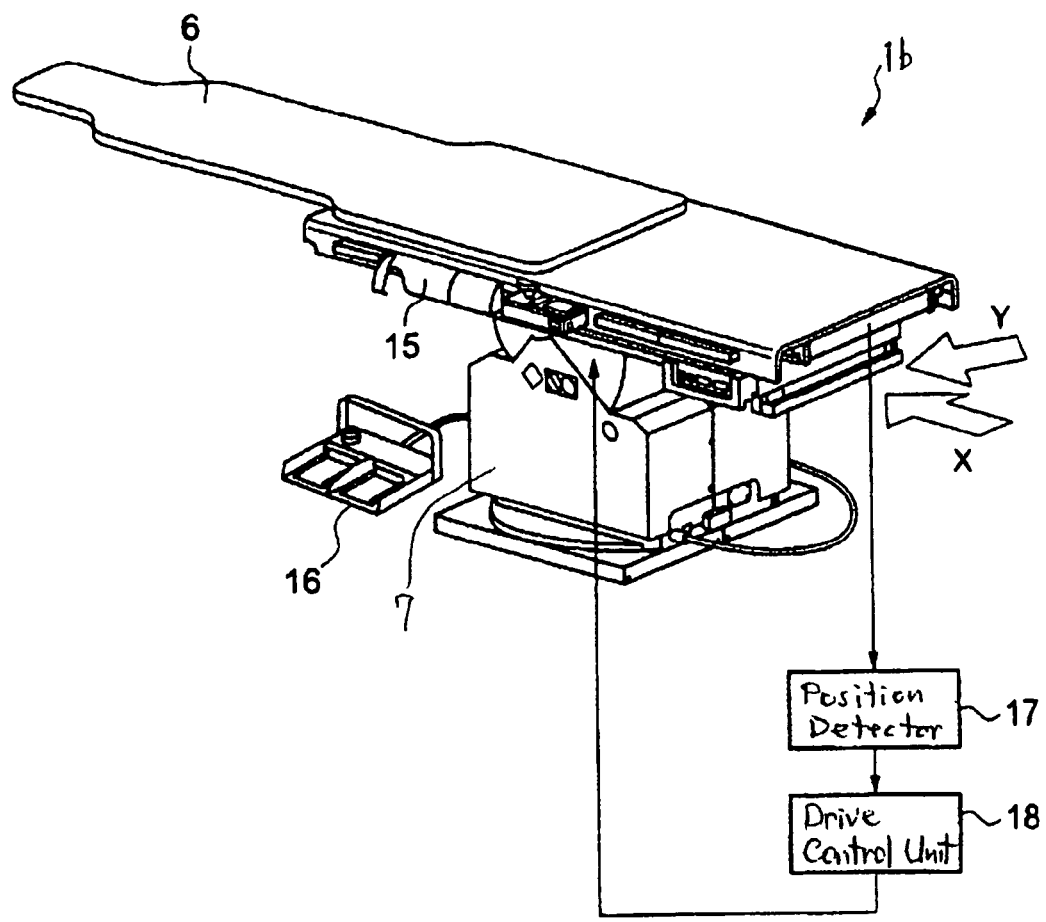
FIG. 2 is a schematic showing an example of a diagnostic table.

FIG. 2 is a schematic showing an example of the diagnostic table 1b. As shown in FIG. 2, the tabletop 6 can be moved along the longitudinal direction X. The tabletop 6 is typically moved electrically along the longitudinal direction X (i.e., a direction C in FIG. 3A) when the tabletop 6 is tilted, and is typically moved manually when it is horizontally placed. In other words, as described earlier, the tabletop 6 is driven by the gears and the motor provided in the supporting unit 7. The tabletop 6 may alternatively be moved electrically when it is horizontally placed, in a manner similar to when it is tilted. The position detector 17 may be disposed by the tabletop 6, and detected information may be transmitted to the drive control unit 18 provided in the supporting unit 7. The diagnostic table 1b may also include the operation unit 15 and the foot switch 16.

Also as described earlier, the tabletop 6 may be tilted to orient a patient's left side up and right side down, and vice versa, when the patient is lying along the longitudinal direction of the tabletop 6, in addition to or instead of tilting the tabletop 6 to orient a patient's head up and feet down, and vice versa. In this case, the tabletop 6 may also be moved electrically along the lateral direction of the tabletop 6 (i.e., a direction D in FIG. 3A) when the tabletop 6 is tilted. In other words, similar to the movement along the longitudinal direction X, the tabletop 6 is driven by gears and a motor which would be provided in the supporting unit 7, and held by a magnetic brake and a tooth clutch.

Figure 3A:
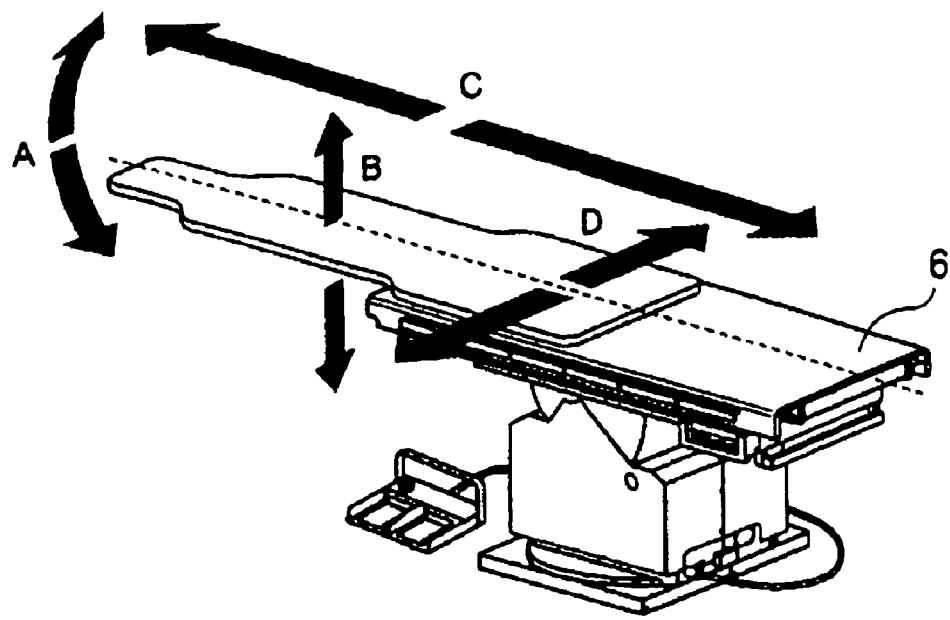
FIGS. 3A and 3B are schematics showing examples of movements of a tabletop.
Figure 3B:
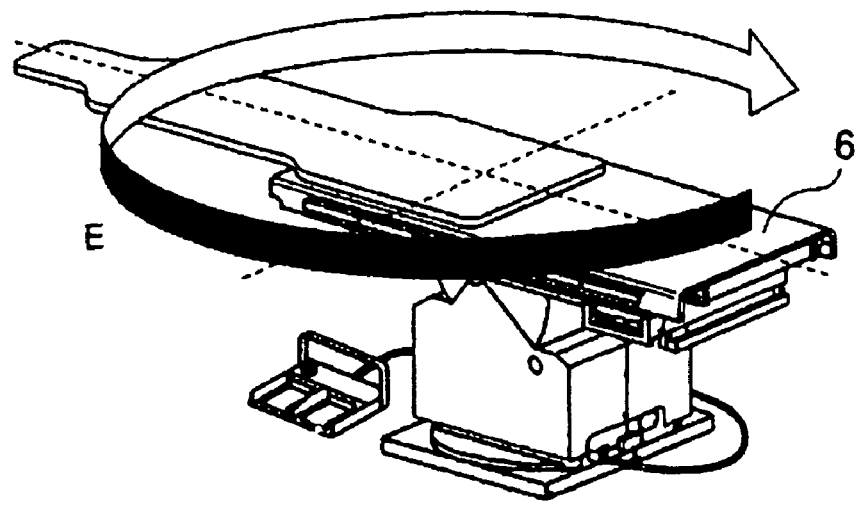

FIGS. 3A and 3B show examples of movement of the tabletop 6. As shown in FIG. 3A, the tabletop 6 can be tilted to orient a patient's head up and feet down, and vice versa (A), and also be moved upwards and downwards (B). The tabletop 6 can also be moved along the longitudinal direction (C) and the lateral direction (D). As shown in FIG. 3B, the tabletop 6 can also be rotated as in the panning operation (E).

Details of the tabletop 6 and a stopper for preventing the tabletop 6 from sliding unintentionally are now described with reference to FIGS. 4A to 7.

Figure 4B:
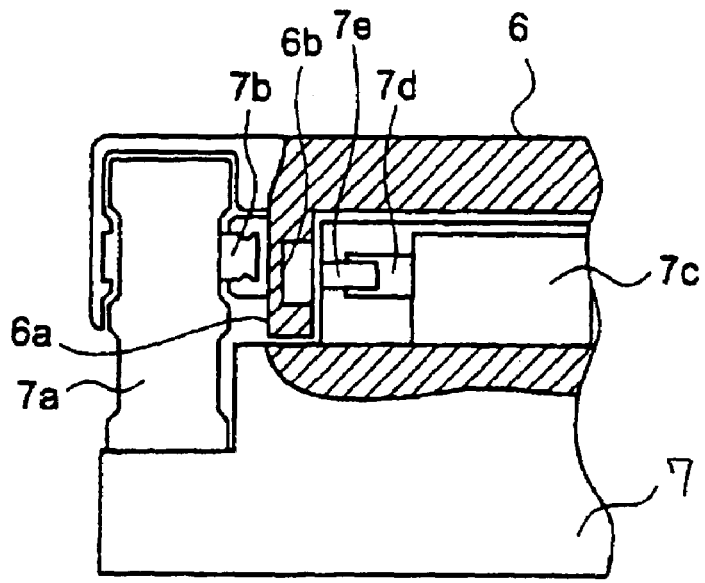
FIGS. 4A and 4B are enlarged views showing an exemplary configuration of the tabletop and a stopper for preventing the tabletop from sliding unintentionally.
Figure 4A:
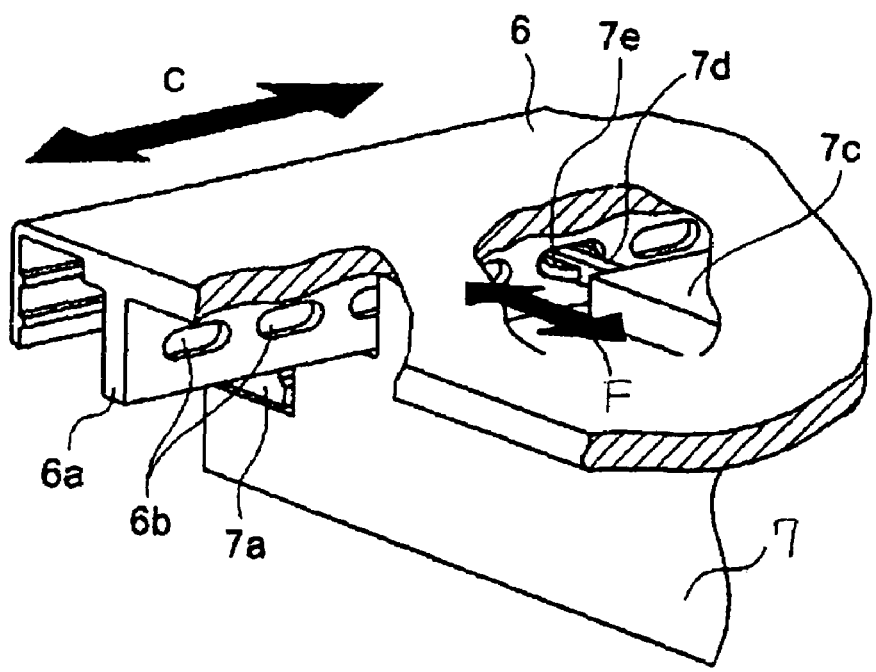

FIG. 4A is an enlarged view showing an exemplary configuration of the tabletop 6 and the stopper when the diagnostic table 1b is viewed from a direction Y shown in FIG. 2. FIG. 4B is an enlarged view showing an exemplary configuration of the tabletop 6 and the stopper when the diagnostic table 1b is viewed from the direction X shown in FIG. 2.

As shown in FIG. 4A, the tabletop 6 has a convex portion 6a on the side opposite to the side on which the patient lies. The convex portion 6a is provided along the direction C. The convex portion 6a has a plurality of oval-shape indentations 6b along the direction C. In other words, since the tabletop 6 is tilted in a manner that one end of the tabletop 6 is lifted while the other end is lowered, the indentations are provided along the portion of the tabletop 6 to be lifted. The tabletop 6 can be tilted such that one side of the tabletop 6 corresponding to, for example, the patient's left side is lifted while the other side corresponding to, for example, the patient's right side is lowered, by providing similar indentations along the direction D shown in FIG. 3A, that is, along the portion of the tabletop 6 to be lifted. And a similar stopper for preventing the tabletop 6 from sliding along the direction D may also be provided. The shape of the indentations 6b may alternatively be round, quadrangular, or any other possible shape. The indentations 6b may be provided, but are required to be provided, at predetermined intervals.

The supporting unit 7 includes a supporting member 7a and a guide rail 7b as shown in FIG. 4B. The convex portion 6a is slidably supported along the direction C at one side of the supporting member 7a provided on the top surface at one end of the supporting unit 7 through the guide rail 7b. The supporting unit 7 also includes the stopper for preventing the tabletop 6 from unintentionally sliding along the direction C. The stopper includes a solenoid 7c which has an excitation coil. The solenoid 7c is energized to move a movable iron core 7d as a projecting portion, so that the movable iron core 7d is moved into one of the indentations 6b along a direction F. Also, the movable iron core 7d can be removed from the one indentation 6b along the direction F. The movable iron core 7d is to be understood to be an example of a protruding portion to be inserted into one of the indentations 6b. The solenoid 7c is understood to be an example of a driving unit to move the protruding portion. For example, a plate, board, or lump like shape material may alternatively be used as the protruding portion.

The movable iron core 7d may have a roller 7e at its one end to be inserted into one of the indentations 6b. This roller 7e may help the movable iron core 7d to be smoothly inserted into one the indentations 6b.

Figure 5:
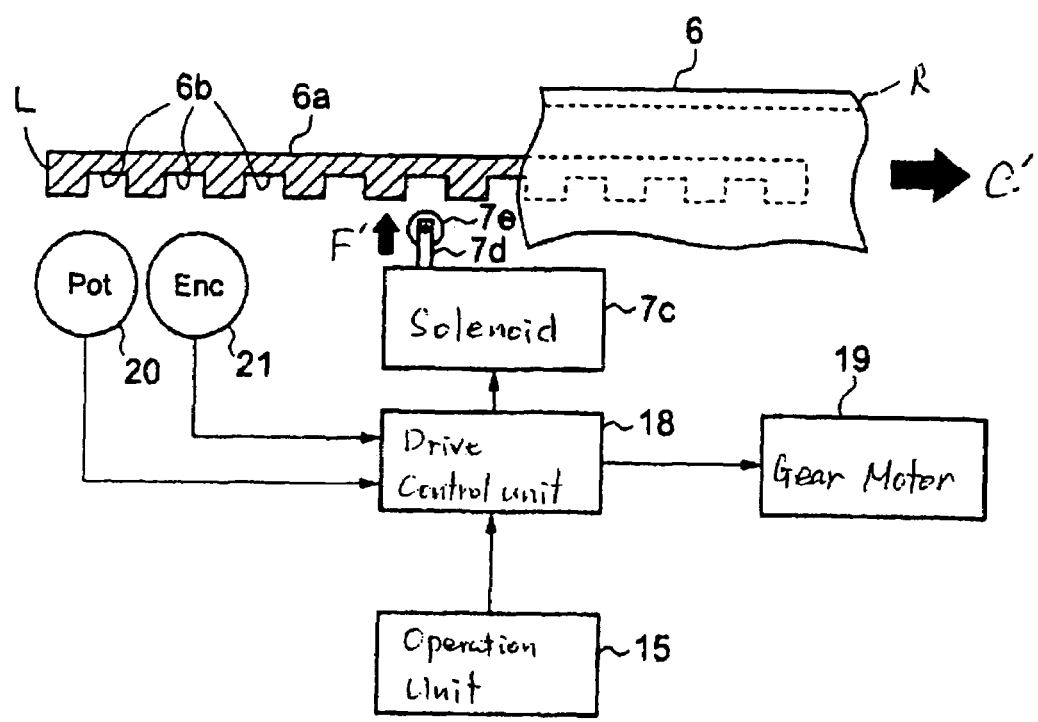
FIG. 5 is a schematic showing a relationship between the tabletop and the stopper.

FIG. 5 is a schematic showing a relationship between the tabletop 6 and the stopper. The supporting unit 7 also includes a gear motor 19 which acts as the gear motor described above. The gear motor 19 is controlled by the drive control unit 18, in response to instructions from the operation unit 15.

The supporting unit 7 further includes a potentiometer 20 and an encoder 21 used to detect that the tabletop 6 is unintentionally sliding when the tabletop is tilted. Although one of the potentiometer 20 and the encoder 21 may be used to achieve the above purpose, both may be used such that the remaining one of the potentiometer 20 and the encoder 21 may be used in the event that one of the potentiometer 20 and the encoder 21 malfunctions. Since the diagnostic table 1b is usually equipped with the position detector 17 which may also include one or more potentiometers and encoders, the position detector 17 may be used as the potentiometer 20 and the encoder 21. The potentiometer 20 is typically suitable for detecting a slide of a relatively larger distance (e.g., one hundred millimeters (100 mm)) of the tabletop 6. Conversely, the encoder 21 is typically suitable for detecting a slide of a relatively smaller distance (e.g., five millimeters (5 mm)) of the tabletop 6.

Before radiography of the patient on the tabletop 6, the operator usually operates the operation unit 15 to tilt the tabletop 6. For example, one end L of the tabletop 6 is lifted while the other end R is lowered. In this case, the tabletop 6 is usually held at a predetermined position by the magnetic brake and the tooth clutch, as described above. The tabletop 6 can slide in a direction C' along the longitudinal direction C if there is deficiency in the gear provided under the tabletop 6, the tooth clutch, or the gear motor 19. Also the tabletop 6 may unintentionally slide in the direction C' if one or more fasteners, such as screws or bolts fixing the guide rail 7b, becomes loosened, damaged, or fails.

First Case

When the tabletop 6 starts to slide in the direction C', the potentiometer 20 and the encoder 21 detect a certain amount of movement of the tabletop 6. The detected amount is provided to the drive control unit 18. The drive control unit 18 determines whether any instruction is received or not from the operation unit 15 to move the tabletop 6 along the direction C. In other words, the drive control unit 18 determines whether or not to activate the gear motor 19 in response to the operation unit 15 or any other proper instruction.

If the drive control unit 18 has determined that no instruction is received or no activation instruction is made, the drive control unit 18 controls the solenoid 7c to move the movable iron core 7d towards the tabletop 6 (in a direction F').

Figure 6A:
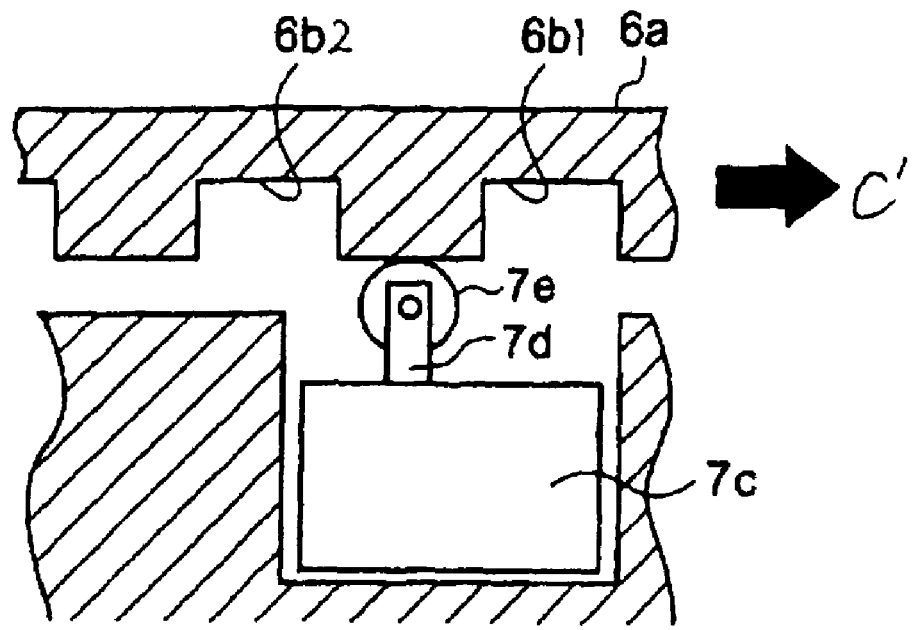
FIGS. 6A and 6B are enlarged views showing an example of insertion of a movable iron core including a roller into an indented portion defined in the tabletop.
Figure 6B:
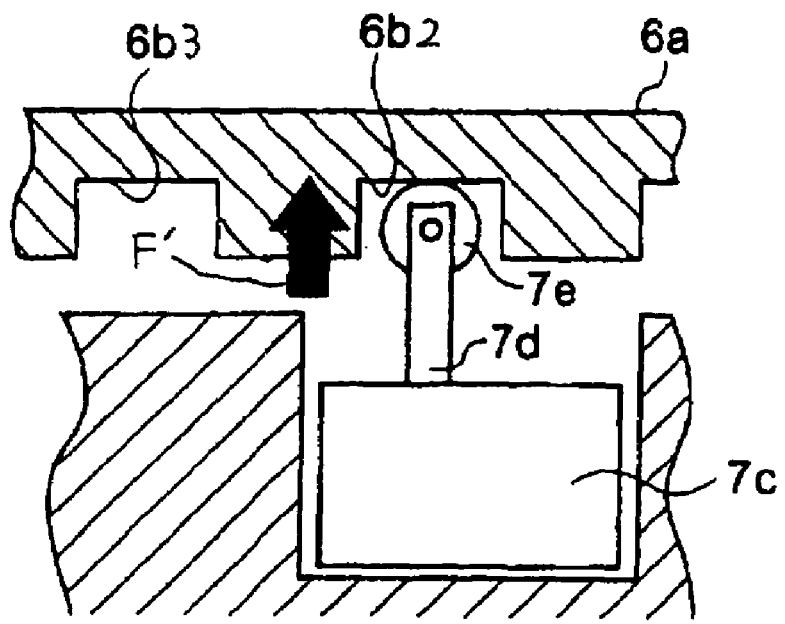

The solenoid 7c provides a predetermined voltage to the excitation coil (not shown) to generate a magnetic force which can linearly move the movable iron core 7d. The movable iron core 7d is protruded or extended to be inserted into one of the indentations 6b provided at the convex portion 6a. FIGS. 6A and 6B show an example of the insertion of the movable iron core 7d with the roller 7e into the indentations 6b.

When the movable iron core 7d is protruded or extended, if it is positioned between the first indentation 6b1 and the second indentation 6b2 of the indentations 6b, the roller 7e smoothly rolls along the convex portion 6a even though the movable iron core 7d and the roller 7e are urged towards the convex portion 6a because of the magnetic force by the solenoid 7c. Since the tabletop 6 slides in the direction C', the movable iron core 7d and the roller 7e are inserted into the second indentation 6b2 (in the direction F') after rolling between the first indentation 6b1 and the second indentation 6b2. Therefore, the tabletop 6 is prevented from sliding further. If the depth of the indentations 6 is too shallow, the roller 7e may roll out of the second indentation 6b2 towards the third indentation 6b3. On the other hand, if it is too deep, the patient lying on the tabletop 6 may feel an uncomfortable bump when the movable iron core 7d and the roller 7e are inserted into the second indentation 6b2. Therefore, the depth of the indentations 6b may be determined, taking the above criteria into consideration. The shape and/or the depth of each indentation may or may not be identical, in addition to their intervals.

Second Case

When the tabletop 6 starts to slide in the direction C', the potentiometer 20 and the encoder 21 detect a certain amount of movement of the tabletop 6. The detected amount is provided to the drive control unit 18. The potentiometer 20 and the encoder 21 can also detect information of direction of such amount of movement. If the drive control unit 18 has determined that an instruction is received from the operation unit 15 or an activation instruction is given to the gear motor 19 in order to move the tabletop 6 along the longitudinal direction C but not in the direction C', the drive control unit 18 controls the solenoid 7c to protrude or extend or extend the movable iron core in the direction F'.

In this case, the instruction is given to move the tabletop 6 upwards along the longitudinal direction C, that is, in a direction opposite to the direction C'. Since the one end L of the tabletop 6 is lifted while the other end R is lowered, the tabletop 6 slides down in the direction C'. Therefore, the movable iron core 7d is controlled to protrude or extend or extend in the direction F'.

Third Case

When the tabletop 6 starts to slide in the direction C', the potentiometer 20 and the encoder 21 detect a certain amount of movement of the tabletop 6. The detected amount is provided to the drive control unit 18. The potentiometer 20 and the encoder 21 can also detect information of direction of such amount of movement. Even if the drive control unit 18 has determined that an instruction is received from the operation unit 15 or an activation instruction is given to the gear motor 19 in order to move the tabletop 6 along the longitudinal direction C and in the direction C', the drive control unit 18 may determine to control the solenoid 7c to protrude or extend the movable iron core in the direction F'.

For example, when a rotation speed of the gear motor 19 is predetermined or determined in response to an instruction from the operation unit 15, the drive control unit 18 instructs the gear motor 19 to rotate at the determined rotation speed when or before the drive control unit 15 controls to activate the gear motor 19. The gear motor 19 informs the drive control unit 18 of its actual rotation speed (or currently rotating speed). When the drive control unit 18 receives information of the actual rotation speed from the gear motor 19, the drive control unit 18 compares the actual rotation speed to the instructing rotation speed. If the actual rotation speed is faster than the instructing rotation speed, the drive control unit 18 determines that the tabletop 6 is sliding unintentionally in the direction C' even if the instruction is given to move the tabletop 6 in the direction C'.

This is the case that the instruction is given to move the tabletop 6 downwards along the longitudinal direction C, that is, in the direction C'. Since, however, the one end L of the tabletop 6 is lifted while the other end R is lowered and the tabletop 6 slides down in the direction C', the tabletop 6 is moving faster than instructed. Therefore, the movable iron core 7d is controlled to protrude or extend in the direction F'.

In any of cases including, but not limited to, the above three cases, the operator may help the patient to leave the tabletop 6 after the examination. The operator may analyze the reason of the slide, and, if possible, find and implement a solution for the problem. At any appropriate time, whether it is before the patient leaves the tabletop 6 or after the solution has been implemented, the operator may operate the operation unit 15 to tilt back the tabletop 6 to a horizontal position. The operator can release the engagement between the second indentation 6b2 and the movable iron core 7d by operating a release lever (not shown) for releasing the movable iron core 7d from the magnetic force by the solenoid 7c and manually pushing the movable iron core 7d back to its initial position. Accordingly, the tabletop 6 can be moved back to its original position and/or can be used again if the solution is implemented.

Instead of the manual operation of releasing the engagement between the second indentation 6b2 and the movable iron core 7d, the movable iron core 7d may automatically be moved back to its initial position. For example, when the operator operates the operation unit 15 to tilt back the tabletop 6 to the horizontal position, the potentiometer 20 and the encoder 20 detect that the tabletop 6 is positioned horizontally. The drive control unit 18 receives the detected information from the potentiometer 20 and the encoder 21, and controls the solenoid 7c to retract the movable iron core 7d (in a direction opposite to the direction F'). The solenoid 7c provides a predetermined voltage to the excitation coil in a reverse direction to generate a magnetic force which can linearly retract the movable iron core 7d. Accordingly, the movable iron core 7d is released or removed from second indentation 6b2. In this case, the operator operates the operation unit 15 to tilt back the tabletop 6 to the horizontal position so that the tabletop 6 can be moved back to its original position and/or can be used again if the solution is implemented.

If the tabletop 6 does not slide at all when it is tilted, the tabletop 6 is moved back to its original (horizontal) position. In response to the potentiometer 20 and the encoder 21 detecting the horizontal position, the engagement of the tooth clutch is released in the supporting unit 7. Also the magnetic brake is ready to be released again to allow the floating operation and the panning operation. The operator may or may not perform the floating operation and/or the panning operation, and accordingly the patient can leave the tabletop 6.

As described above, if the tabletop 6 slides unintentionally when it is tilted, the potentiometer 20 and the encoder 21 immediately detect the slide. In response to the detection, the drive control unit 18 controls the solenoid 7c to protrude or extend or extend the movable iron core 7d so that the movable iron core 7d can be inserted in to one of the indentations 6b. Accordingly, this ensures that the tabletop 6 is prevented from sliding. The safety of the patient is maintained.

In addition, since the stopper for preventing the tabletop 6 from sliding has a relatively simple structure as a protruding portion such as, for example, the movable iron core 7d for insertion into one of the indentations 6b provided at the tabletop 6, the tabletop 6 can be assuredly prevented from sliding. Further, by changing shapes and/or rigidity of the protruding portion and the indentations 6b, the load to be supported by the protruding portion inserted into one of the indentations 6 can be changed.

In the embodiment, even if the tabletop 6 is not tilted in a manner that one side of the tabletop 6 corresponding to, for example, the patient's left side is lifted while the other side corresponding to, for example, the patient's right side is lowered, it is possible to provide similar indentations along the direction D shown in FIG. 3A and a similar stopper for preventing the tabletop 6 from sliding along the direction D.

Although the plurality of indentations 6b have been described as being engaged with the protruding portion, a plurality of through holes may be provided in the convex portion 6a instead of the plurality of indentations 6b.

Figure 7:
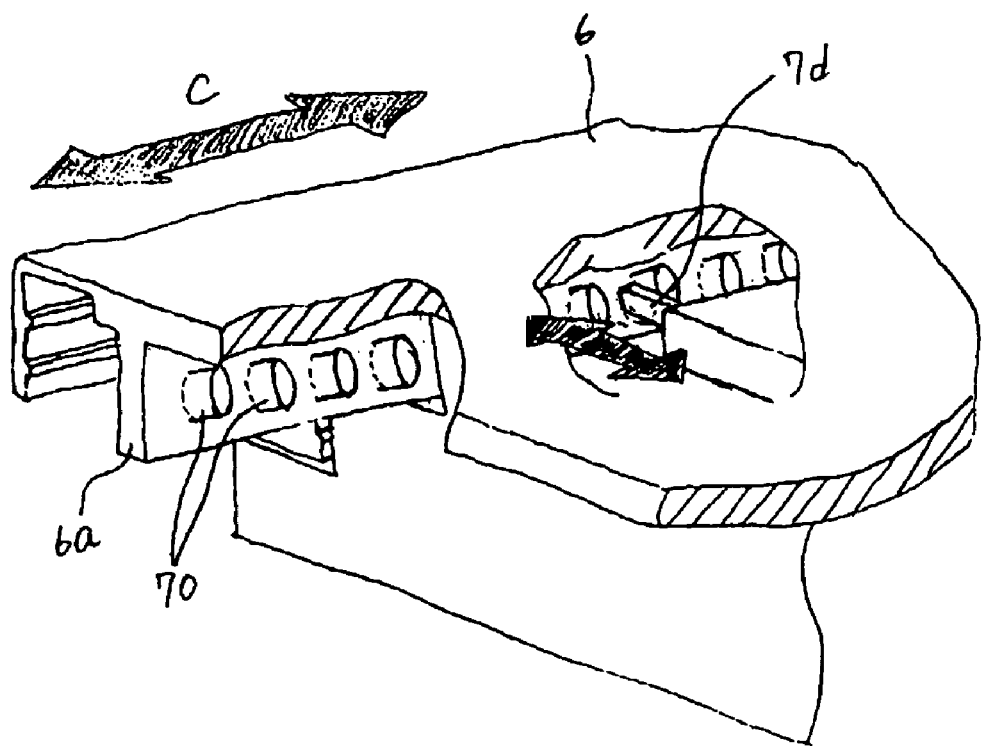
FIG. 7 is a schematic showing another exemplary configuration of the tabletop and the stopper.

Further, as shown in FIG. 7, the plurality of indentations 6 may alternatively be replaced with a plurality of convexities (or second protruding portions) 70. When the plurality of convexities 70 are provided at the convex portion 6a, for example, along the longitudinal direction C (along the portion of the tabletop 6 to be lifted), the protruding portion such as, for example, the movable iron core 7d can be hooked to one of the plurality of convexities 70, such that the movable iron core 7d cooperates with the convexity 70. The roller 7e is not required to be used with the movable iron core 7d. The shape of the convexities 70 is not limited to a column shown in FIG. 7, but may be formed in any shape.

The convex portion 6a having the indentations, through holes, convexities, or any other similarly functional mechanism may be provided at only one longitudinal side of the tabletop 6 or at both longitudinal sides of the tabletop 6. Also, the stopper for preventing the tabletop 6 from sliding, such as, for example, the solenoid 7c and the movable iron core 7d can be provided in a corresponding manner. This can also be applied to prevent the tabletop 6 from sliding along the lateral direction D shown in FIG. 3A.

Figure 8:
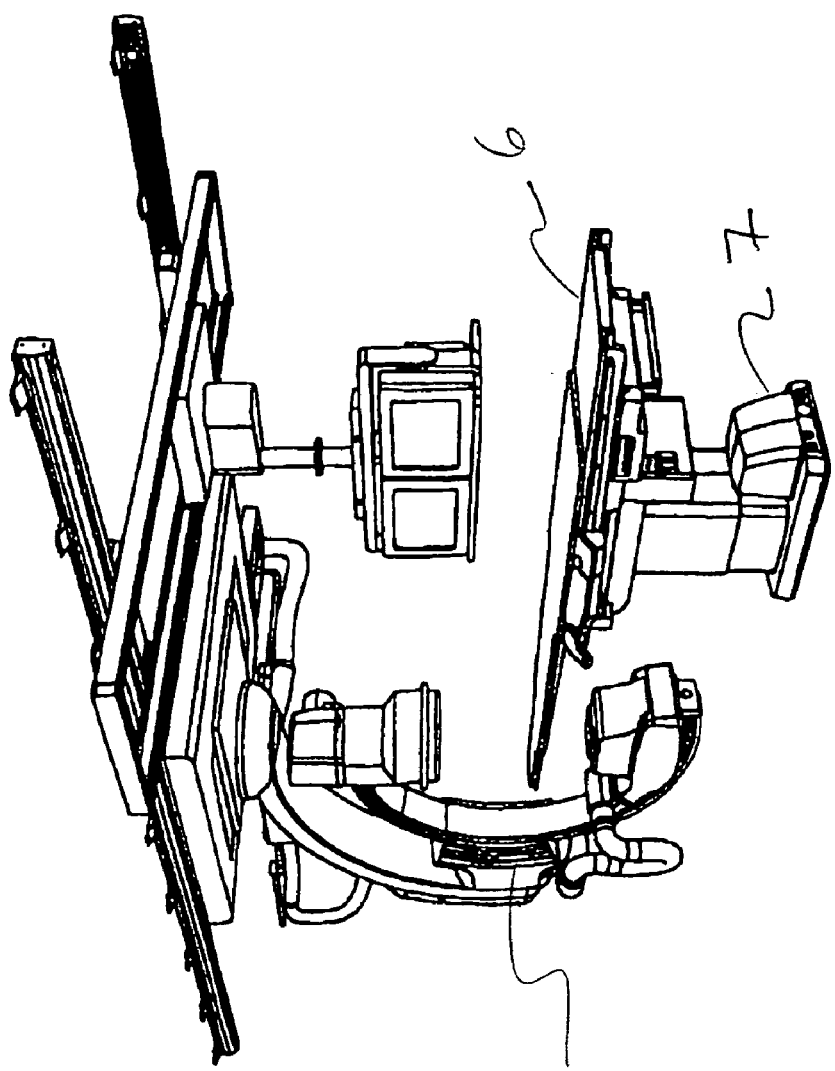
FIG. 8 is a schematic showing an example of another X-ray diagnosis apparatus.

FIG. 8 is a schematic showing an example of another X-ray diagnosis apparatus. When the X-ray diagnosis apparatus is used for the examination in which a flow of a contrast agent is controlled in accordance with a force of gravitation, the X-ray diagnosis apparatus as shown in FIG. 8 may be more suitable for controlling the flow of the contrast agent in accordance with the force of gravitation. The X-ray diagnosis apparatus shown in FIG. 8 includes only one imaging unit having, for example, a C-arm with an X-ray tube at its one end and an X-ray detector at the other end. The imaging unit may move along rails fixed to the ceiling. Such a configuration with one imaging unit moving along rails fixed to the ceiling can allow the operator to easily adjust the X-ray tube and the X-ray detector to a target position of the patient even when a tabletop is moved and tilted. Similar mechanisms and controls of the tabletop 6 and the supporting unit 7 described for the X-ray diagnosis apparatus shown in FIG. 1 can be applied to this X-ray diagnosis apparatus shown in FIG. 8.

The embodiment described above is not limited to the X-ray diagnosis apparatus for the examination in which a flow of a contrast agent is controlled in accordance with a force of gravitation. The embodiment described above can also be applied to a diagnostic table for an X-ray diagnosis apparatus to be used for any other purposes and to such an X-ray diagnosis apparatus. Further, the embodiment described above can be applied to a diagnostic table for any medical imaging apparatus, which includes tilting the diagnostic table, as well as a medical imaging apparatus including such a diagnostic table.

Numerous modifications and variations of the present invention are possible in light of the above teachings. It is therefore to be understood that within the scope of the appended claims, the invention may be practiced otherwise than as specifically described herein.

The invention claimed is:

1. A diagnostic table for a medical imaging apparatus, the table comprising:
   a supporting unit;
   a tabletop movably supported by the supporting unit;
   a sliding command input device configured to receive a sliding command input, and generate a sliding command instruction corresponding to the sliding command input;
   a driving device configured to slidably move the tabletop in response to the sliding command instruction;
   a detector configured to detect actual sliding movement of the tabletop;
   a controller configured to compare the actual sliding movement of the tabletop with the sliding command instruction, the controller being configured to generate a fault condition instruction when the actual sliding movement of the tabletop is inconsistent with the sliding command instruction; and
   a stopper provided on the supporting unit and configured to be activated in response to the fault condition instruction in order to inhibit sliding movement of the tabletop.

2. The diagnosis table according to claim 1, wherein the controller is configured to generate the fault condition instruction when actual sliding movement of the tabletop is detected by the detector but no sliding command instruction was generated by the sliding command input device.

3. The diagnosis table according to claim 2, wherein:
   the sliding command input device is configured to receive a sliding direction command input, and generate a sliding direction command instruction corresponding to the sliding direction command input;
   the detector is configured to detect a direction of actual sliding movement of the tabletop; and
   the controller is configured to compare the direction of actual sliding movement of the tabletop with the sliding direction command instruction, the controller being configured to generate the fault condition instruction when the direction of actual sliding movement of the tabletop is inconsistent with the sliding direction command instruction.

4. The diagnosis table according to claim 3, wherein:
   the sliding command input device is configured to receive a sliding speed command input, and generate a sliding speed command instruction corresponding to the sliding speed command input;
   the detector is configured to detect a speed of actual sliding movement of the tabletop; and
   the controller is configured to compare the speed of actual sliding movement of the tabletop with the sliding speed command instruction, the controller being configured to generate the fault condition instruction when the speed of actual sliding movement of the tabletop is inconsistent with the sliding speed command instruction.

5. The diagnosis table according to claim 4, wherein:
   the driving device is a motor;
   the detector is configured to detect a speed of actual sliding movement of the tabletop; and
   the controller is configured to compare the speed of actual sliding movement of the tabletop with a maximum speed at which the motor is configured to slide the tabletop, the controller being configured to generate the fault condition instruction when the speed of actual sliding movement of the tabletop is greater than the maximum speed at which the motor is configured to slide the tabletop.

6. The diagnosis table according to claim 1, wherein:
   the sliding command input device is configured to receive a sliding direction command input, and generate a sliding direction command instruction corresponding to the sliding direction command input:
   the detector is configured to detect a direction of actual sliding movement of the tabletop; and
   the controller is configured to compare the direction of actual sliding movement of the tabletop with the sliding direction command instruction, the controller being configured to generate the fault condition instruction when the direction of actual sliding movement of the tabletop is inconsistent with the sliding direction command instruction.

7. The diagnosis table according to claim 6, wherein:
   the sliding command input device is configured to receive a sliding speed command input, and generate a sliding speed command instruction corresponding to the sliding speed command input;
   the detector is configured to detect a speed of actual sliding movement of the tabletop; and
   the controller is configured to compare the speed of actual sliding movement of the tabletop with the sliding speed command instruction, the controller being configured to generate the fault condition instruction when the speed of actual sliding movement of the tabletop is inconsistent with the sliding speed command instruction.

8. The diagnosis table according to claim 7, wherein:
   the driving device is a motor;
   the detector is configured to detect a speed of actual sliding movement of the tabletop; and
   the controller is configured to compare the speed of actual sliding movement of the tabletop with a maximum speed at which the motor is configured to slide the tabletop, the controller being configured to generate the fault condition instruction when the speed of actual sliding movement of the tabletop is greater than the maximum speed at which the motor is configured to slide the tabletop.

9. The diagnosis table according to claim 1, wherein:
   the sliding command input device is configured to receive a sliding speed command input, and generate a sliding speed command instruction corresponding to the sliding speed command input;
   the detector is configured to detect a speed of actual sliding movement of the tabletop; and
   the controller is configured to compare the speed of actual sliding movement of the tabletop with the sliding speed command instruction, the controller being configured to generate the fault condition instruction when the speed of actual sliding movement of the tabletop is inconsistent with the sliding speed command instruction.

10. The diagnosis table according to claim 9, wherein:
    the driving device is a motor;
    the detector is configured to detect a speed of actual sliding movement of the tabletop; and
    the controller is configured to compare the speed of actual sliding movement of the tabletop with a maximum speed at which the motor is configured to slide the tabletop, the controller being configured to generate the fault condition instruction when the speed of actual sliding movement of the tabletop is greater than the maximum speed at which the motor is configured to slide the tabletop.

11. The diagnosis table according to claim 1, wherein:
the driving device is a motor;
the detector is configured to detect a speed of actual sliding movement of the tabletop; and
the controller is configured to compare the speed of actual sliding movement of the tabletop with a maximum speed at which the motor is configured to slide the tabletop, the controller being configured to generate the fault condition instruction when the speed of actual sliding movement of the tabletop is greater than the maximum speed at which the motor is configured to slide the tabletop.

12. The table according to claim 1, wherein the tabletop comprises a plurality of first portions, and the stopper comprises a protrusion configured to be inserted into one of the plurality of first portions.

13. The table according to claim 12, wherein the tabletop comprises a plurality of through holes as the plurality of first portions.

14. The table according to claim 12, wherein the tabletop comprises a plurality of indentations as the plurality of first portions.

15. The table according to claim 12, further comprising:
a roller disposed at an end of the protrusion, the roller configured to be disposed in one of the plurality of first portions.

16. The table according to claim 12, wherein the plurality of first portions are provided along a portion of the tabletop to be raised.

17. The table according to claim 12, wherein the protrusion comprises a movable iron core, and the stopper comprises a solenoid configured to move the iron core into and out of the plurality of first portions.

18. The table according to claim 1, wherein the tabletop comprises a plurality of first protrusions, and the stopper comprises a second protrusion configured to cooperate with one of the first protrusions.

19. The table according to claim 18, wherein the plurality of first portions are provided along a portion of the tabletop to be raised.

20. The table according to claim 18, wherein the second protrusion a movable iron core, and the stopper comprises a solenoid configured to move the movable iron core into and out of cooperation with one of the plurality of first protruding portions.

* * * * *